United States Patent [19]
Gaglani et al.

[11] Patent Number: 6,017,955
[45] Date of Patent: Jan. 25, 2000

[54] METHOD OF STABILIZING BIOCIDAL COMPOSITIONS OF HALOALKYNYL COMPOUNDS

[75] Inventors: Kamlesh Gaglani, Belle Mead; Eeva-Liisa Kuusisto; John Hansen, both of Livingston; Ismael Colon, Deville, all of N.J.

[73] Assignee: Troy Technology Corporation, Inc., Wilmington, Del.

[21] Appl. No.: 08/659,743

[22] Filed: Jun. 6, 1996

Related U.S. Application Data

[63] Continuation-in-part of application No. 08/479,220, Jun. 7, 1995, abandoned.

[51] Int. Cl.$^7$ ............................. A01N 47/10; A01N 25/34
[52] U.S. Cl. ........................ 514/478; 514/479; 424/404
[58] Field of Search .................................. 514/478, 479; 424/404

[56] References Cited

U.S. PATENT DOCUMENTS

| | | | |
|---|---|---|---|
| 3,660,499 | 5/1972 | Kobayashi et al. | 260/613 D |
| 3,923,870 | 12/1975 | Singer | 260/482 C |
| 4,259,350 | 3/1981 | Morisawa et al. | 424/308 |
| 4,592,773 | 6/1986 | Tanaka et al. | 71/88 |
| 4,616,004 | 10/1986 | Edwards | 514/63 |
| 4,639,460 | 1/1987 | Rose | 514/369 |
| 4,719,227 | 1/1988 | Schade et al. | 514/452 |
| 4,806,263 | 2/1989 | Leathers et al. | 252/106 |
| 4,915,909 | 4/1990 | Song | 422/28 |
| 4,945,109 | 7/1990 | Rayudu | 514/478 |
| 5,082,722 | 1/1992 | Guglielmo, Sr. | 428/255 |
| 5,209,930 | 5/1993 | Bowers-Daines et al. | 424/401 |

FOREIGN PATENT DOCUMENTS 2138292  8/1983  United Kingdom.

OTHER PUBLICATIONS

International Search Report of PCT/US96/08956 dated Nov. 4, 1996.

*Primary Examiner*—Theodore J. Criares
*Attorney, Agent, or Firm*—Banner & Witcoff, Ltd.

[57] ABSTRACT

This invention is directed to a method for stabilizing a composition which comprises a mixture of a halopropargyl compound. The composition can be used broadly in industrial systems and more particularly with substrates such as paints, coatings, stucco, concrete, stone, cementaceous surfaces, wood, caulking, sealants, textiles, and the like.

21 Claims, 7 Drawing Sheets

METHOD OF STABILIZING BIOCIDAL COMPOSITIONS OF HALOALKYNYL COMPOUNDS

CROSS-REFERENCE TO RELATED APPLICATION

This application is a continuation-in-part application of Application Ser. No. 08/479,220 filed on Jun. 7, 1995 (now abandoned).

BACKGROUND OF THE INVENTION

1. Field of the Invention

This invention is directed to biocidal compositions containing a haloalkynyl compound, and especially a halopropargyl compound. The invention is particularly directed to such compositions containing such compounds which have been stabilized to reduce the loss of biocidal activity due to the degradation of such compounds. The invention is especially directed to the stabilization of compositions containing iodopropargyl carbamates, such as 3-iodo-2-propargylbutyl carbamate.

2. Description of Related Art

Both exterior and interior surfaces and substrates of all types, when exposed to common environmental conditions, e.g. moisture, are prone to attack, discoloration and various kinds of destruction by a variety of species of microorganisms, including fungi, algae, bacteria and protozoa. As a result, there is a great need and requirement for an effective and economical means to protect for extended periods of time both exterior and interior surfaces and various type substrates and commercial formulations from the deterioration and destruction caused by such microorganisms.

Materials which need protection with a suitable antimicrobial composition include stucco, concrete, stone, cementaceous surfaces, wood, caulking, sealants, leather, plastics, textiles, biodegradable compositions including such materials as paints and other coating formulations, surfactants, proteins, starch-based compositions, inks, emulsions and resins as well as numerous other materials and other substances which may be attacked by destructive microbes.

An enormously wide variety of materials have been identified which, to various degrees, are effective is retarding or preventing the growth of, and accompanying destruction caused by, such microbes. Such biocidal compounds include halogenated compounds, organometallic compounds, quaternary ammonium compounds, phenolics, metallic salts, heterocyclic amines, formaldehyde donors, organo-sulfur compounds and the like.

Formulated products that are protected against microbial attack by the inclusion of such biocidal additives must retain their biocidal activity for a prolonged time period to be most useful. Indeed, such products often are used to impart a biocidal activity to another product or to a substrate, such as wood and the like, which itself requires extended protection against microbial attack.

One well-known class of biocides are those containing a halopropargyl moiety, and especially an iodopropargyl moiety. Such compounds are widely disclosed in the patent literature including U.S. Pat. Nos. 3,660,499; 3,923,870; 4,259,350; 4,592,773; 4,616,004 and 4,639,460 to name a few. Included within this class of compounds are the halopropargyl carbamates which are known primarily for their fungicidal activity. 3-iodo-2-propargyl butyl carbamate, hereinafter also referred to as IPBC, is one of the best known and probably the most widely used of the halopropargyl carbamate fungicides. IPBC is a highly active broad spectrum fungicide. In addition to its fungicidal activity, IPBC also has been associated with algaecidal activity. In this regard, Great Britain Patent 2,138,292 and U.S. Pat. Nos. 4,915,909 and 5,082,722 contain such disclosures.

As noted above, the haloalkynyl compounds, including halopropargyl compounds, and especially the halopropargyl carbamates typically are formulated with a variety of other ingredients, in both aqueous and organic solvent mixtures. For various reasons, it is desired that these compositions maintain their biocidal activity for prolonged periods of time. Unfortunately, such compositions have sometimes been observed to experience a progressive loss in such activity. Until now, the reason for such degradation has not been understood. Through experimentation, however, applicants have found that one prevalent cause for the loss of biocidal activity in such formulations is exposure of the haloalkynyl compound to high levels of alkalinity or high levels of acidity. In an aqueous environment, such conditions involve an extreme pH condition, both acidic and basic. Applicants have discovered that by formulating the composition so as to neutralize the acid or alkaline source in the composition, or by buffering the formulation, degradation of the biocidal haloalkynyl compound, including specifically halopropargyl compounds such as IPBC, can be significantly retarded. The invention also helps to ameliorate other problems, such as the formation of lacrimators or corrosion of metal containers, caused by the degradation of IPBC in solvent-based alkyd paint formulations.

BRIEF DESCRIPTION OF THE INVENTION

The present invention is based, therefore, on the surprising discovery of a composition and method for stabilizing the biocidal activity of certain formulations containing a haloalkynyl compound. The invention is specifically directed to a composition and method for stabilizing the biocidal activity of certain formulations containing a halopropargyl compound, and particularly a halopropargyl carbamate fungicide, that due to the present of alkaline or acidic constituents, experiences a decline in biocidal activity with time. There are several aspects of the present invention. In a first aspect, the invention comprises neutralizing excess acid or base in an aqueous composition containing the haloalkynyl compound, respectively, with a base or an acid, as appropriate to adjust the pH of the aqueous preparation of the composition to a pH in the range of 3.0 to 8.0, preferably to a range of 4.0 to 7.7, and more preferably to a range of 5.5 to 7.7. In another aspect, an acidic or basic compound is added to an organic solvent-containing formulation containing a halopropargyl compound such as IPBC, wherein the formulation respectively contains a degradation enhancing level of alkalinity or acidity. In still another aspect, the invention employs a buffer to keep the halopropargyl-containing formulation, either aqueous or organic solvent-based, in the proper pH range, i.e., at an acceptable level of alkalinity or acidity.

Thus, the present invention provides a biocidal composition comprising a mixture of a halopropargyl compound and a buffer, wherein the weight ratio of said halopropargyl compound to said buffer is between 50:1 to 1:100 and wherein said composition is useful for providing biocidal activity to an end-use formulation and stabilizing the end-use formulation at a pH of between 3.0 and 8.0 against degradation of said halopropargyl compound.

The present invention also provides a method of stabilizing a biocidal formulation containing a halopropargyl compound, said formulation having an alkalinity or an acidity sufficient to cause degradation of said halopropargyl compound in the absence of added acid, base or buffer, said method comprising adding a sufficient amount of an acid, a base or a buffer to said formulation to adjust the pH of said formulation to within the range of 3.0 to 8.0.

The present invention also comprises a method of providing an end-use formulation with biocidal activity comprising adding a sufficient amount of a mixture of a halopropargyl compound and a buffer, wherein the weight ratio of said halopropargyl compound to said buffer in said mixture is between 50:1 to 1:100, to said end-use formulation to impart biocidal activity to said formulation and provide said formulation with a pH within the range of 3.0 to 8.0.

DETAILED DESCRIPTION OF THE INVENTION

The present invention is directed to a composition and a method for stabilizing certain formulations containing a haloalkynyl compound. The invention is specifically directed to a composition and a method for reducing the degradation of halopropargyl compounds, particularly a halopropargyl carbamate such as IPBC, in aqueous- or organic solvent-based formulations, caused by a presence of a degradation causing amount of alkalinity or a degradation causing amount of acidity, such as a high (alkaline) or low (acidic) pH condition. The degradation of the active halopropargyl compound results in a loss of biocidal activity. The present invention is particularly aimed at a way for protecting biocidal halopropargyl compounds, and especially iodopropargyl carbamates, against degradation by acidic and basic environments. The invention thus provides for stabilized compositions containing a biocidal halopropargyl compound.

A halopropargyl compound for use in the present invention can be identified by the following structure:

wherein Y is a halogen, preferably iodine and X can be (1) oxygen which is part of an organic functional group; (2) nitrogen which is part of an organic functional group; (3) sulfur which is part of an organic functional group; or (4) carbon which is part of an organic functional group.

The functional group of which oxygen is a part is preferably an ether, ester, or carbamate group. The functional group of which nitrogen is a part is preferably an amine, amide, urea, nitrile, or carbamate group. The functional group of which sulfur is a part is preferably a thiol, thiane, sulfone, or sulfoxide group. The organic functional group of which carbon is a part is preferably an ester, carbamate or alkyl group.

Examples of compounds which may be used as the halopropargyl compound of this invention are especially the fungicidally active iodopropargyl derivatives. In this regard, please see U.S. Pat. Nos. 3,923,870, 4,259,350, 4,592,773, 4,616,004, 4,719,227, and 4,945,109, the disclosures of which are herein incorporated by reference. These iodopropargyl derivatives include compounds derived from propargyl or iodopropargyl alcohols such as the esters, ethers, acetals, carbamates and carbonates and the iodopropargyl derivatives of pyrimidines, thiazolinones, tetrazoles, triazinones, sulfamides, benzothiazoles, ammonium salts, carboxamides, hydroxamates, and ureas. Preferred among these compounds is the halopropargyl carbamate, 3-iodo-2-propynyl butyl carbamate (IPBC). This compound is included within the broadly useful class of compounds having the generic formula:

Wherein R is selected from the group consisting of hydrogen, substituted and unsubstituted alkyl groups having from 1 to 20 carbon atoms, substituted and unsubstituted aryl, alkylaryl, and aralkyl groups having from 6 to 20 carbon atoms and from substituted and unsubstituted cycloalkyl and cycloalkenyl groups of 3 to 10 carbon atoms, and m and n are independently integers from 1 to 3, i.e., m and n are not necessarily the same.

Particularly preferred are formulations of such halopropargyl carbamates where m is 1 and n is 1 having the following formula:

Suitable R substituents include alkyls such as methyl, ethyl, propyl, n-butyl, t-butyl, pentyl, hexyl, heptyl, octyl, nonyl, decyl, dodecyl, octadecyl, cycloalkyls such as cyclohexyl, aryls, alkaryls and aralkyls such as phenyl, benzyl, tolyl, cumyl, halogenated alkyls and aryls, such as chlorobutryl and chlorophenyl, and alkoxy aryls such as ethoxyphenyl and the like.

Especially preferred are such iodopropargyl carbamates as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof.

The amount of the halopropargyl compound in ultimate formulations which are stabilized in accordance with the present invention can vary widely and an optimum amount generally is affected by the intended application and other components of a particular formulation. In any event, generally such formulations contain anywhere from about 0.001 to about 20 percent by weight of such halopropargyl compound. Usually, such formulations contain from 0.01 to 10 percent by weight of such compounds. Such formulations, protected against microbial attack by the inclusion of a halopropargyl carbamate, can be prepared from highly concentrated compositions of the halopropargyl active ingredients, such as by appropriate dilution. Oftentimes, the optimum useful range is about 0.1% to 1.0% of halopropargyl carbamate in a final formulation. Upon the use of such formulations in end use systems, it is possible to protect surfaces as well as other substrates for extended periods of time against microbial growth, for example, from both algae and fungi.

Compositions of the present invention will generally be formulated by mixing the halopropargyl active ingredient or a concentrate of the halopropargyl compound in a liquid vehicle for dissolving or suspending the active component. The vehicle also may contain a diluent, an emulsifier and a wetting-agent. Common uses of these biocidal compositions include protection of wood, paints and other coatings, adhesives, paper, textiles, plastics, cardboard, lubricants, caulkings, and the like. An extensive list of potential industries and applications for the present invention can be found in U.S. Pat. No. 5,209,930 which is herein incorporated by reference. Compositions containing the halopropargyl compound fungicide, particularly an iodopropargyl carbamate such as IPBC, are often formulated as liquid mixtures, but may be provided as wettable powders, dispersions, or in any other suitable product type which is desirable and most useful. In this regard, formulations to be stabilized against degradation of the active halopropargyl biocide in accordance with the present invention can be provided as ready-for-use products in the form of aqueous or organic solvent solutions, dispersions, oil solutions and dispersions, emulsions, aerosol preparations and the like or as a concentrate.

Useful liquid vehicles, including organic solvents, for the halopropynyl compound, particularly the preferred iodopropynyl butyl carbamate are water, alcohols, such as methanol, butanol and octanol, glycols, several glycol ethers like propylene glycol n-butyl ether, propylene glycol tert-butyl ether, 2-(2-methoxymethylethoxy)-tripropylene glycol methyl ether, propylene glycol methyl ether, dipropyleneglycol methyl ether, tripropylenelene glycol methyl ether, propylene glycol n-butyl ether and the esters of the previously mentioned compounds. Other useful solvents are n-methyl pyrrolidone, n-pentyl propionate, 1-methoxy-2-propanol, dibasic esters of several dicarboxylic acids and mixtures thereof, such as the dibasic isobutyl ester blend of succinic, glutaric and adipic acids, aromatic hydrocarbons, such as xylene and toluene, high aromatic petroleum distillates, e.g., solvent naphtha, distilled tar oil, mineral oils, ketones such as acetone, and petroleum fractions such as mineral spirits and kerosene. Other suitable organic solvents are well known to those skilled in the art.

When preparing formulations of the present invention for specific applications, the composition also will likely be provided with other adjuvants conventionally employed in compositions intended for such applications such as organic binding agents and polymers, such as alkyd resins, additional fungicides, auxiliary solvents, processing additives, fixatives, driers, such as cobalt octoate and cobalt naphthenate, plasticizers, UV-stabilizers or stability enhancers, water soluble or water insoluble dyes, color pigments, siccatives, corrosion inhibitors, antisettlement agents, anti-skinning agents and the like. Additional fungicides used in the composition are preferably soluble in the liquid vehicle.

Stabilized compositions of the present invention may also be an aqueous, latex-based product such as acrylic, vinyl acetate acrylic, polyvinyl acetate, styrene-butadiene and silicone emulsions. They may also be microemulsions or microemulsion concentrates.

According to the present invention, substrates are protected from infestation, for example by fungal and algal organisms, simply by treating said substrate with a formulation containing a halopropargyl compound and stabilized in accordance with the present invention. Such treating may involve mixing the composition with the substrate, coating or otherwise contacting the substrate with the composition and the like. As noted above, representative applications include paints, stains and other coatings, leather-treatment fluids, wood treatment compositions, metal-working fluids, water treatment, e.g., cooling water, adhesive, sealants, personal care products, paper coatings and many others.

Formulations prone to halopropargyl degradation which are stabilized in accordance with the present invention are those compositions having an excess of either an alkaline or an acidic component such that the composition has a high alkalinity or acidity, but does not necessarily have to be either excessively acidic or basic. For aqueous formulations, such compositions are easily identified by a simple measurement of the pH of the aqueous phase of the composition. Formulations having a pH of above 8.0, in more preferred practice having a pH above about 7.8, and in most preferred practice having a pH above about 7.5, to a varying extent are prone to halopropargyl degradation. Such formulations can be stabilized by the addition of an acid or a suitable buffer. Alternatively, compositions having a pH of below 3.0, in preferred practice compositions having a pH below about 4.0, in more preferred practice having a pH below 5.5, and in most preferred practice having a pH below about 6.5 also are prone, to a varying extent, to halopropargyl degradation. Again, such formulations can be stabilized, in this case, by the addition of a base or a suitable buffer. For organic formulations, compositions which are susceptible to halopropargyl degradation due to the presence of an excess of alkaline or acidic components can be identified by treating a measured quantity of the formulation with an equal mass of water and measuring the pH of the aqueous phase. As above, formulations tested in this manner that produce an aqueous phase having a pH of 8.0 and above, preferably above about 7.8, and more preferably above about 7.5, or an aqueous phase having a pH below 3.0, preferably below about 4.0, and more preferably below 5.4 demonstrate a greater tendency to exhibit halopropargyl degradation and can be stabilized by the addition, respectively, of an acid or a base or by the addition of a suitable buffer. Consequently, when used throughout the specification and claims, pH is intended to be applicable to both aqueous-based and organic solvent-based compositions as noted above, such that the use of a pH in the specification and claims is not intended to exclude organic solvent-based formulations.

In certain alkyd-containing formulations that are used as coatings and wood preservatives, the use of drying agents (catalysts that promote or affect the reaction of the alkyd with oxygen) may further lead to IPBC instability. This problem is particularly encountered in formulations employing cobalt driers, which are generally acidic in nature. For example, a typical alkyd formulation might include 20–25% by weight of an alkyd resin, 65–75% by weight of a mineral spirit solvent, 0–5% of a co-solvent such as methoxypropylacetate, 0 to 1% of an antiskinning agent such as methyl ethyl ketoxim, 0 to 1% of an antisettlement additive such as bentonite clay, 0.1 to 1% of a drier such as cobalt octoate, up to 4% by weight of a dye and pigment and 0.1 to 5% of IPBC. To compensate for the acidic character of the cobalt drier, as well as other driers that are commonly used with alkyds, the present invention provides the conjoint use of a basic co-drier (including a buffer such as Calcium-10). In this way, the formulation is stabilized against IPBC degradation without significantly changing the drying properties of the alkyd formulation. Whereas, calcium driers (including basic calcium driers) have been used extensively in organic solvent-based alkyd paints, the use of these materials in a formulation also containing a halopropargyl compound, such as IPBC, to stabilize the biocidal composition, has not been recognized.

According to one aspect of the method of the invention, there is added to the halopropargyl-containing composition a sufficient amount of an acid or base, as appropriate, to adjust the pH of an aqueous mixture of the composition to a stabilizing pH, or there is added a sufficient amount of a suitable buffer to keep the formulation in the desired pH range. As used in the context of the present invention, a stabilizing pH is a pH in the range of 3.0 to 8.0, preferably in the range of 4.0 to 7.7, more preferably in the range of 5.5 to 7.7, and most preferably in the range of 5.5 to 7.5. For aqueous formulations having an excess of acidic or alkaline components, the quantity of base, acid or buffer to be added is easily determined by routine experimentation analogous to an acid-base titration. The appropriate reagent for stabilizing the formulation, i.e., an acid, a base or a buffer, is slowly added to a measured sample of the aqueous formulation, absent such an additive, while monitoring the pH change. Once the relative amount of reagent needed to adjust the aqueous formulation to a pH in the range of 3.0 to 8.0, preferably in the range of 4.0 to 7.7, and more preferably in the range of 5.5 to 7.7, has been determined, the same relative amount of acid, base or buffer, as appropriate, is added to the complete formulation to stabilize it against degradation of the halopropargyl compound. For organic (non-aqueous) formulations, the same procedure can be used except that initially an aqueous test composition must be prepared by thoroughly mixing a measured amount of the formulation with an equal mass of water. The procedure thereafter parallels the procedure outlined above for assessing the appropriate treatment level for aqueous formulations.

The use of an appropriate buffer, added to ensure that the formulated product remains in the appropriate pH range, has an advantage that an excess of the buffering material can be used without taking the formulation into an undesirable pH range. Thus, there is no close criticality in the total amount added, as long as at least a sufficient amount of buffer is added to prevent the degradation caused by the level of acidity or alkalinity in the formulation. The use of a buffer has an additional important advantage. Any strong acid or strong base that might be formed under the conditions of using the formulated product also would be countered by the continuing presence of additional buffer added into the formulated product.

Thus, a particularly important aspect of the present invention relates to novel combinations of materials, such as solutions, dispersions, emulsions, and powders of IPBC and weakly basic materials, such as auxiliary driers (calcium, barium, etc.), salts of organic acids, etc., or buffers that can be sold as distinct products to be used in end-use formulations and provide the pesticidal (biocidal) stability in the end-use formulation. Alternatively, the invention can be employed by adding the appropriate buffer or pH neutralizing material to the end-use formulation that contains the IPBC.

Suitable acids which can be used to adjust the pH of compositions containing an excess of an alkaline component include organic acids such as formic acid, acetic acid, propionic acid, glutaric acid, 2-ethyl hexanoic acid, methane sulfonic acid, lactic acid, p-toluene sulfonic acid and the like, and inorganic acids such as hydrochloric acid, sulfuric acid, phosphoric acid, boric acid and the like. Suitable bases include the organic bases, preferably tertiary amines, such as trimethylamine, triethylamine, triethanolamine, triisopropanolamine and the like, and the inorganic bases such as the alkali metal hydroxides, including sodium hydroxide and ammonium hydroxide, and alkali metal carbonates. It is preferred to use relatively weak acids and relatively weak bases to make the above-noted pH adjustment.

As noted above, it is often preferred to use a suitable buffer, i.e., a material that simultaneously functions as both a weak acid and a weak base, which is able to react with (i.e., neutralize,) both stronger acids and stronger bases. Suitable buffers include bicarbonates, carbonate esters, complex carbonate salts of organic acids, hydrogen phosphates, phosphate esters, phosphinate esters, borates, borate esters, hydrogen sulfates, sulfinates, and sulfate esters. Specific examples of suitable buffers include potassium bicarbonate, potassium biphthalate, potassium bisulfate, potassium dihydrogen citrate, dipotassium hydrogen citrate, potassium dihydrogen phosphate, dipotassium hydrogen phosphate, potassium hydrogen tartrate, potassium hydrogen oxolate, potassium hydrogen maleate, potassium hydrogen succinate, potassium hydrogen glutarate, potassium hydrogen adipate, potassium tetraborate, potassium pentaborate, potassium octaborate and all the corresponding sodium salts, complex calcium carbonate salts of organic acids (such as octanoic acid, iso-octanoic acid, 2-ethyl hexanoic acid, hexanoic acid, and the like), 2-[2-amino-2-oxoethyl)amino]ethanesulfonic acid, N-[2-acetamido]-2-aminoethanesulfonic acid, N,N-bis [2-hydroxyethyl]-2-aminoethanesulfonic acid, 2-[bis(2-hydroxyethyl)amino]ethanesulfonic acid, and other similar materials known in the art.

As noted above, the acid, base or buffer is added to a formulation containing a halopropargyl compound which in the absence of such additive would exhibit a level of alkalinity or a level of acidity composition that would cause the premature degradation of the halopropargyl compound,. The acid, base or buffer is added in a sufficient amount to counteract such acidic or alkaline components by adjusting the pH of the formulation containing the halopropargyl compound to within the pH stable range of 3.0 to 8.0, preferably to within the range of 4.0 to 7.7, and more preferably to a pH between 5.5 and 7.7. Such pH can be measured directly in an aqueous preparation of the halopropargyl compound, or can be measured in a similar fashion in organic solvent-based compositions after appropriate treatment with water.

Generally, stabilized compositions, including both concentrated preparations and fully formulated products are likely to contain 0.1 to 50 weight percent, more usually 1 to 40 weight percent and most often 1 to 25 weight percent of the active halopropargyl biocide, 0.1 to 20 weight percent, more usually 1 to 15 weight percent and most often 1 to 10 weight percent of the acid, base or buffer, for adjusting the pH, and the balance of a solvent or liquid carrier; the total amount of these three components being equal to 100 weight percent, i.e., the sum of the halopropargyl biocide, the acid, base or buffer for pH adjustment and the solvent or liquid carrier constituting the total composition for purpose of these percentages. As noted above, however, fully formulated components will also contain other ingredients, especially those contributing to an excess alkalinity or acidity in the composition in the absence of the pH adjustment.

A particularly preferred aspect of the present invention relates to a composition containing a halopropargyl compound and a buffer, as described above, which can be sold as a concentrate and which is useful as the biocidal additive for introducing the halopropargyl compound, and especially IPBC, into both acidic and alkaline end-use formulations for providing a stable biocidal activity. Generally, such a concentrate comprises a mixture of the halopropargyl compound and a buffer in a weight ratio of halopropargyl compound to buffer in the range of 50:1 to 1:100. Such a concentrate is useful for imparting biocidal activity to the end-use formulation while producing a formulated product having a pH between about 3.0 and 8.0, preferably between about 4.0 and 7.7, and more preferably between 5.5 and 7.7. As used throughout the specification and claims, the term "end-use formulation" is intended to embrace the wide variety of formulations which have used halopropargyl compounds for imparting biocidal activity including paints, stains and other coatings, leather-treatment fluids, wood treatment compositions, metal-working fluids, water treatment, adhesives, sealants, personal care products, paper coatings, paper, textiles, plastics, cardboard, lubricants, caulkings, and the like. An extensive list of potential applications falling within the scope of the term "end-use formulation" can be found in U.S. Pat. No. 5,209,930 which is herein incorporated by reference.

The following examples are presented to illustrate and explain the invention. Unless otherwise indicated, all references to parts and percentages are based on weight.

EXAMPLES

The following comparative examples illustrate the degradation-producing effect caused by excess alkaline components, i.e., excessive alkaline conditions, on compositions (samples) containing iodopropargyl butyl carbamate (IPBC). The samples were subjected to accelerated age testing by maintaining them at 45° C. while monitoring the residual amount of IPBC every week for over a month. The test is believed to be approximately equivalent to one year's aging at room temperature conditions. The level of residual IPBC in the composition was monitored by high performance liquid chromatography (HPLC). A Waters 712 WISP instrument was used for the analysis with a Waters 486 UV detector, and an Alltech Econosphere column (25 cm by 0.46 cm) with C-18 RP packing ($5\mu$). The mobile phase was a mixture of acetonitrile and water in a volume ratio of 6:4. The mobile phase was flowed through the column at a rate of 1 ml/min and the detector wavelength was set at $\lambda$=230 nm. All pH's were measured using a Beckman $\Phi$34 pH meter.

Comparative Example 1

Figure 1:
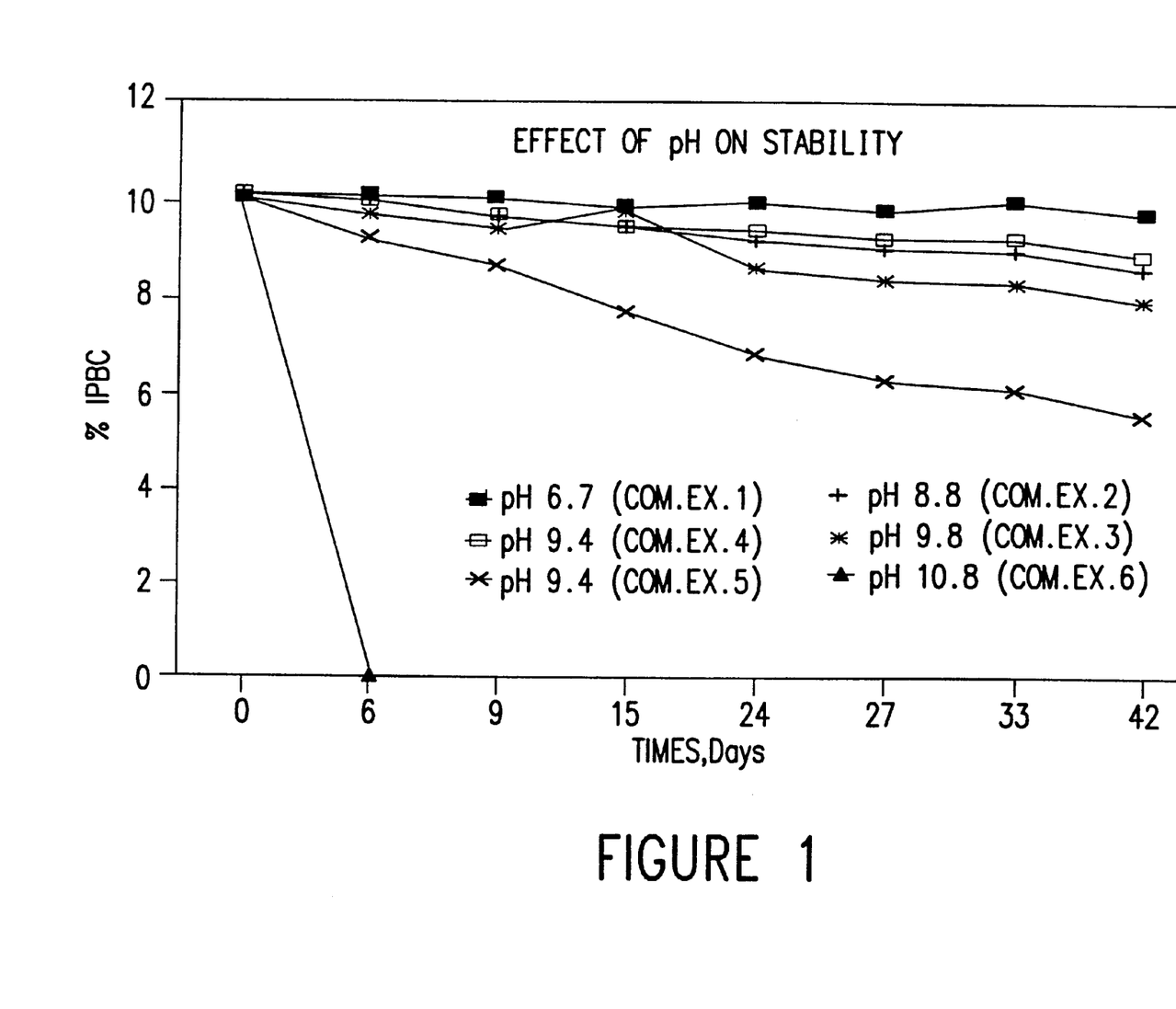
FIG. 1 through FIG. 7 graphically present the stability of the formulations of Comparative Examples 1 through 7 and Examples 1 through 6.

This example constituted a control for the aged alkaline samples. A solution containing 10% IPBC was prepared by dissolving 5.0 g IPBC in a mixture of 42.5 g methanol and 2.5 g of water. The solution had an initial pH of 6.7. FIG. 1 presents the level of residual IPBC over time.

Comparative Example 2

Figure 2:
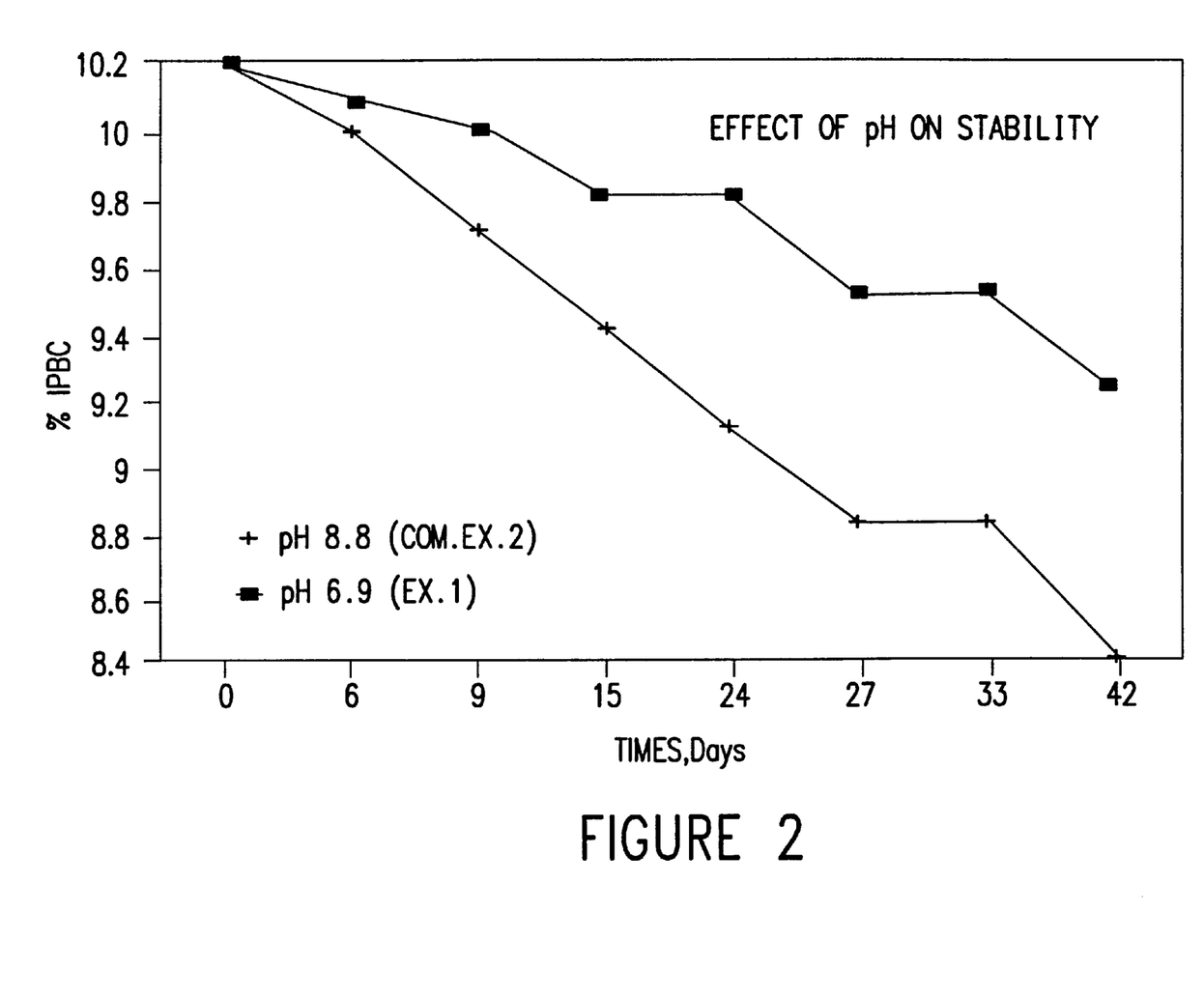

A 10% solution of IPBC was prepared by dissolving 5.0 g IPBC in a mixture of 1.0 g of the tertiary amine Barlene 12 [N-alkyl($C_{12}$–$C_{16}$)-N,N-dimethylamine], 41.4 g methanol and 2.5 g water. The composition had an initial pH of 8.8. FIGS. 1 and 2 illustrate the residual IPBC content of this composition over time.

Comparative Example 3

Figure 3:
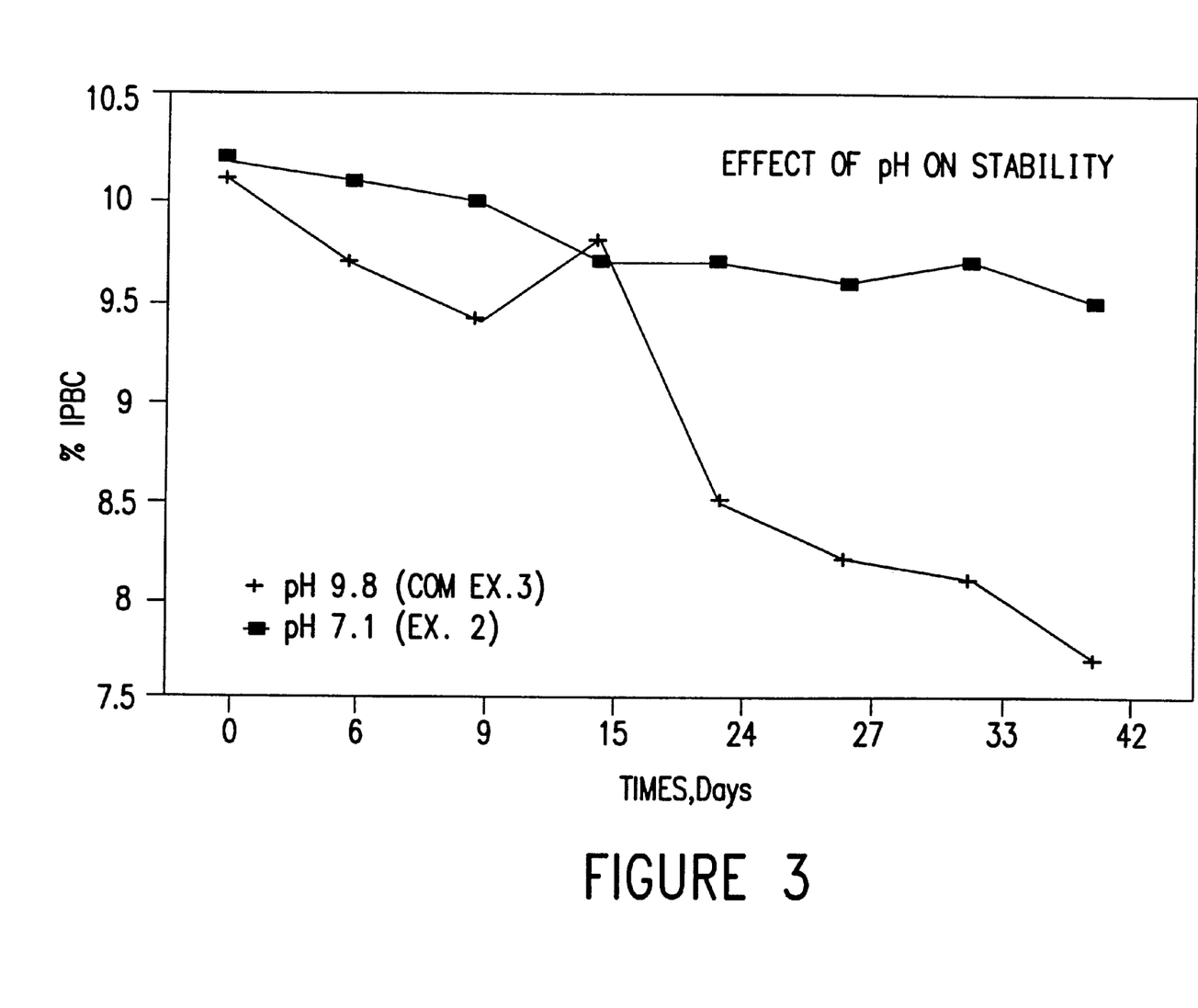

A 10% solution of IPBC was prepared by dissolving 5.0 g IPBC in a mixture of 1.05 g of 2-amino-2-methyl-1-propanol (AMP-95, Angus), 41.5 g methanol and 2.45 g water. The composition had an initial pH of 9.8. FIGS. 1 and 3 illustrate the residual IPBC content of this composition over time.

Comparative Example 4

Figure 4:
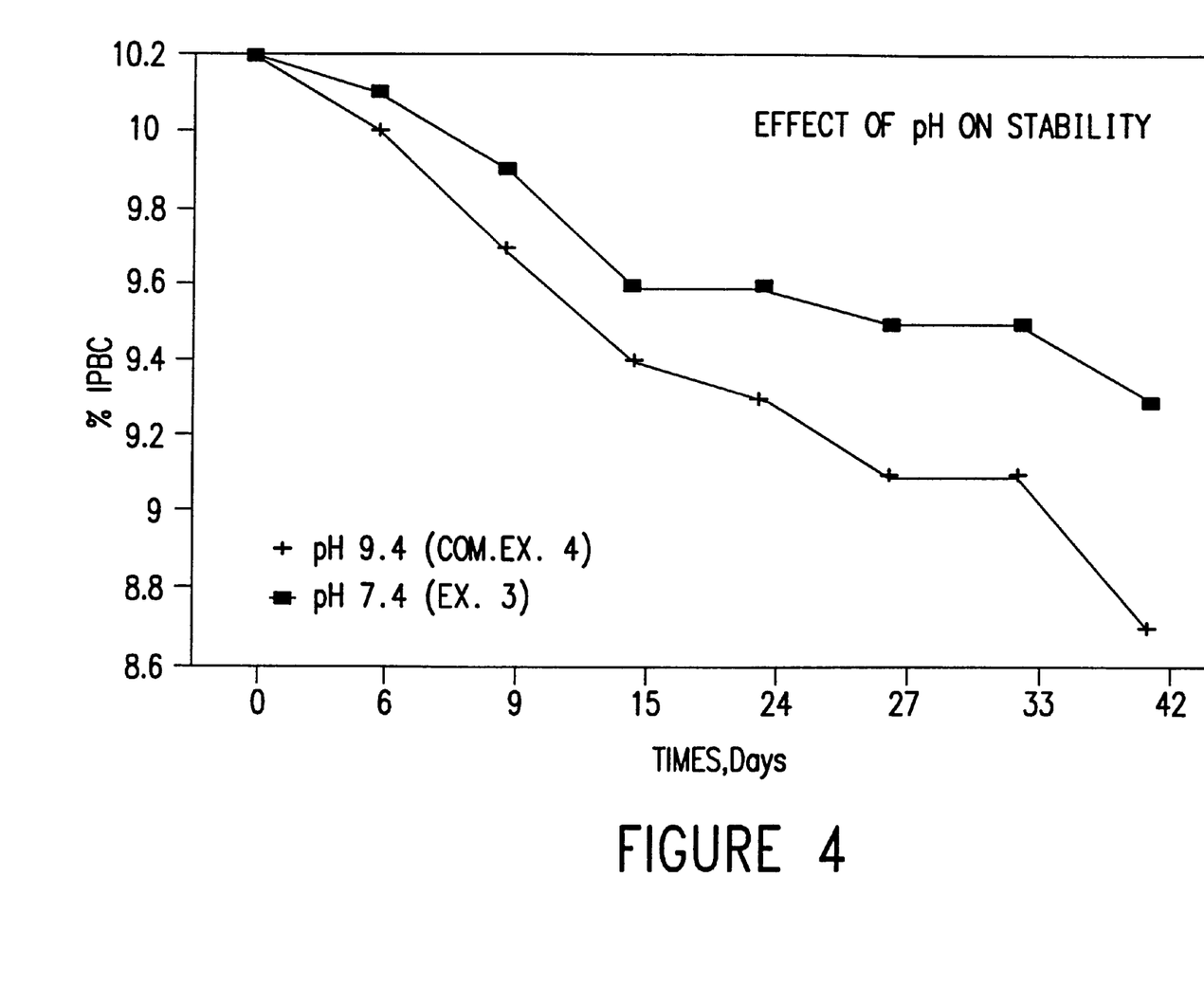

A 10% solution of IPBC was prepared by dissolving 5.0 g IPBC, 1.0 g of the tertiary amine, N,N-dimethyl-ethanol amine, 41.5 g methanol and 2.5 g water. The composition had an initial pH of 9.4. FIGS. 1 and 4 illustrate the residual IPBC content of this composition over time.

Comparative Example 5

Figure 5:
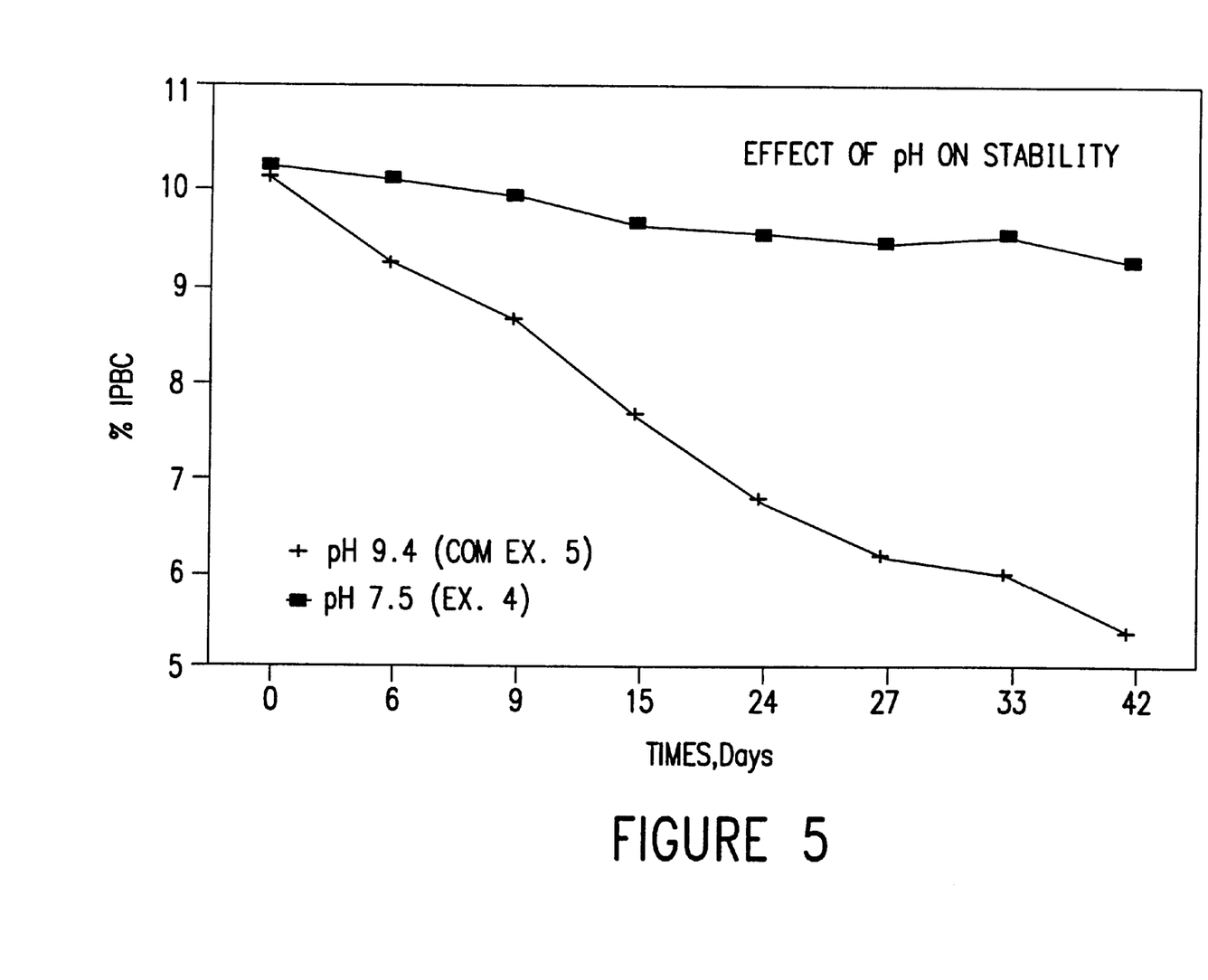

A 10% solution of IPBC was prepared by dissolving 5.0 g IPBC, 1.0 g ammonium hydroxide, 42.2 g methanol and 1.8 g water. The composition had an initial pH of 9.4. FIGS. 1 and 5 illustrate the residual IPBC content of this composition over time.

Comparative Example 6

Figure 6:
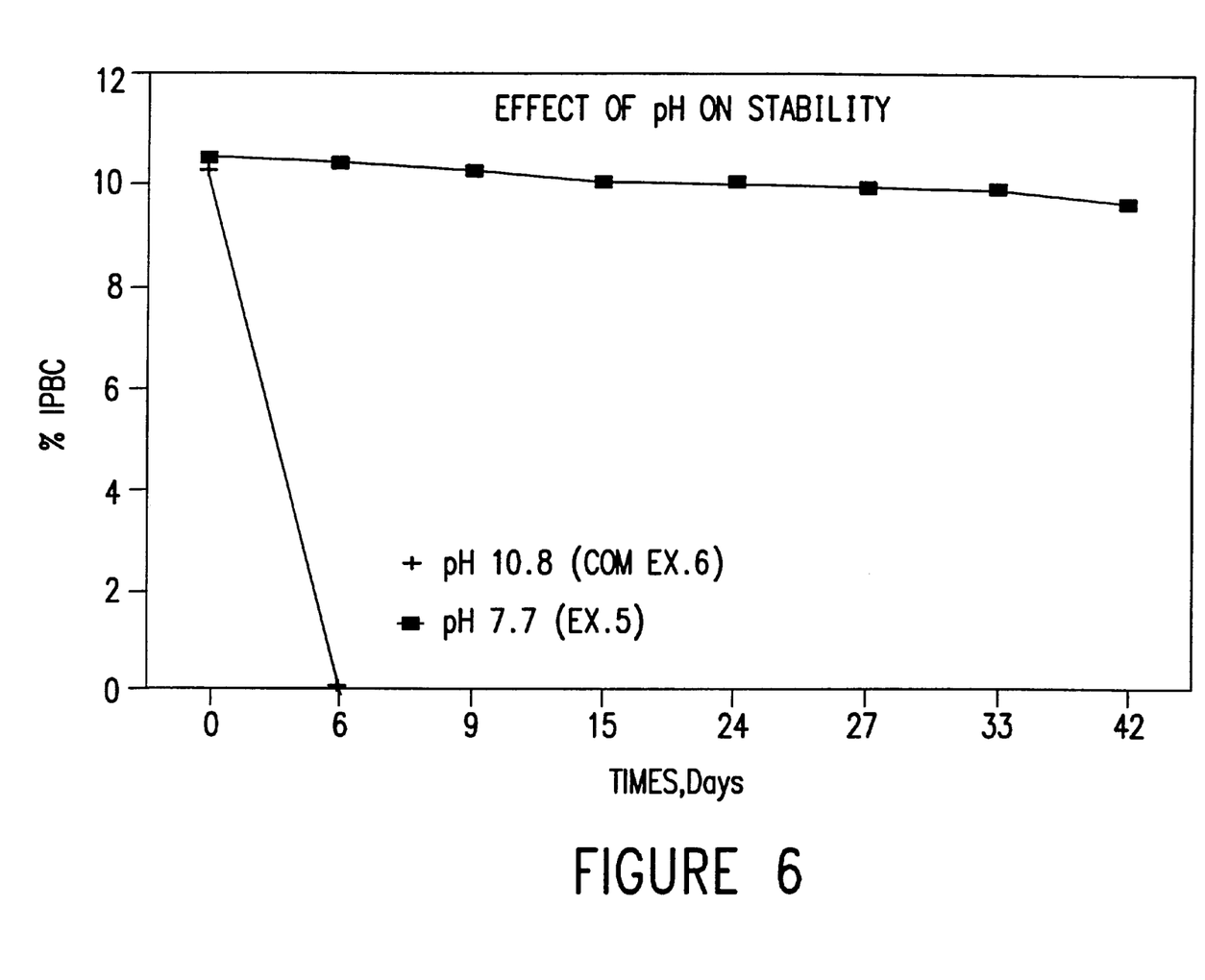

A 10% solution of IPBC was prepared by dissolving 5.0 g IPBC, 0.5 g sodium hydroxide, 42.0 g methanol and 2.5 g water. The composition had an initial pH of 10.8. FIGS. 1 and 6 illustrate the residual IPBC content of this composition over time.

Example 1

A 10% solution of IPBC was prepared by codissolving 5.0 g IPBC, 1.0 g of Barlene 12, 41.1 g methanol 0.4 g acetic acid and 2.5 g water. The resulting composition had a pH of 6.9. FIG. 2 contrasts the stability (residual IPBC content) over time of this composition relative to the composition of Comparative Example 2.

Example 2

A 10% solution of IPBC was prepared by codissolving 5.0 g IPBC, 1.05 g of AMP-95, 40.7 g methanol 0.8 g acetic acid and 2.45 g water. The resulting composition had a pH of 7.1. FIG. 3 contrasts the stability (residual IPBC content) over time of this composition relative to the composition of Comparative Example 3.

Example 3

A 10% solution of IPBC was prepared by codissolving 5.0 g IPBC, 1.0 g N,N-dimethyl-ethanol amine, 40.7 g methanol 0.8 g acetic acid and 2.5 g water. The resulting composition had a pH of 7.4. FIG. 4 contrasts the stability (residual IPBC content) over time of this composition relative to the composition of Comparative Example 4.

Example 4

A 10% solution of IPBC was prepared by codissolving 5.0 g IPBC, 1.0 g ammonium hydroxide, 41.08 g methanol 1.12 g acetic acid and 1.8 g water. The resulting composition had a pH of 7.5. FIG. 5 contrasts the stability (residual IPBC content) over time of this composition relative to the composition of Comparative Example 5.

Example 5

A 10% solution of IPBC was prepared by codissolving 5.0 g IPBC, 0.5 g sodium hydroxide, 40.67 g methanol 0.83 g acetic acid and 2.5 g water. The resulting composition had a pH of 7.7. FIG. 6 contrasts the stability (residual IPBC content) over time of this composition relative to the composition of Comparative Example 6.

Comparative Example 7

Figure 7:
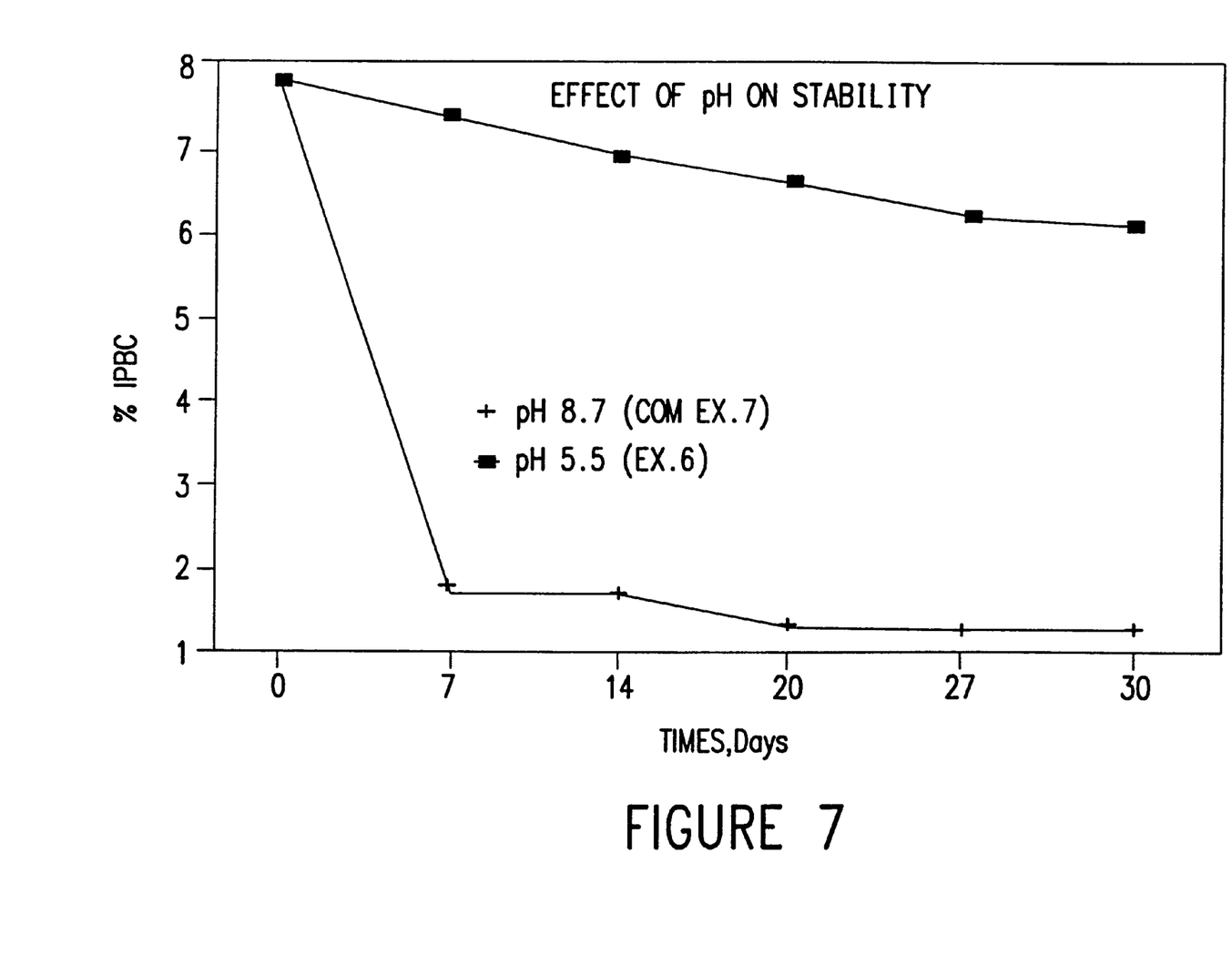

A widely used composition for treating wood was prepared as follows. A mixture of 81.0 g of Bardac 2280 (a quaternary ammonium compound sold by Lonza, Inc.) and 19.0 g of Troysan Polyphase AF-1® brand IPBC (a product commercially available from Troy Chemical Corporation containing 40% by weight IPBC was stirred until a homogeneous solution was obtained. The resulting composition had a pH of 8.7. FIG. 7 presents the residual IPBC content of this composition over time.

Example 6

For comparison with the composition of Comparative Example 7, a mixture of 80.0 g Bardac 2280, 19 g of Troysan Polyphase AF-1® brand IPBC and 1.0 g acetic acid was prepared by mixing these ingredients until a homogeneous solution was obtained. FIG. 7 contrasts the stability (residual IPBC content) over time of this composition relative to the composition of Comparative Example 7.

In both Comparative Example 7 and Example 6, the products were heat aged at 45° C. for over a one month period and the residual IPBC content of the composition was analyzed weekly by HPLC as above.

The data presented in FIGS. 1–7 demonstrate the degradation caused by alkaline pH conditions in aqueous compositions containing IPBC and the degradation-retarding results obtained by acid neutralization.

Examples 7a–p

A series of tests (factorial experimental design) were conducted to evaluate the effects of several compositional variables on the stability of IPBC in solvent-based alkyd paints. The base formulation contained 20% of the alkyd resin, 76.5% mineral spirits, 3% POLYPHASE® P-20T; 0.06% of the acidic cobalt drier (when used- cobalt octoate) or 0.06% of the basic cobalt drier (Cobalt 21) or 0.1 % of Permadry® (Cobalt/Calcium (Co/Ca)) drier available from Troy Chemical Corporation, or 0.18% Troymax® CZ69 (Cobalt/Zirconium (Co/Zr)) drier available from Troy Chemical Corporation and 0.2% methyl ethyl ketoxim (MEKO) (an antiskin agent) when used. Five formulation variables were explored: type of alkyd resin (one with an acid value of 5.6 (low acid) and one with an acid value of 8.0 (high acid)); level of zirconium drier used (0.06% and 0.23%); the type of cobalt drier used (acidic vs. basic vs. Co/Ca vs. Co/Zr); order of addition of the drier components (i.e., which drier is added first); and the optional addition of MEKO. The various compositions were heat aged at 40° C. for 30 days, and the resulting levels of active IPBC (on a residual percentage basis) in the heat-aged formulations are reported below in Tables 1 and 2. These results show that the presence of acidic components had an adverse effect on IPBC stability and that the presence of alkaline materials improved the IPBC stability in these acidic formulations.

Example 8

In this experiment the conditions of Example 7a were repeated with the exception that a buffer having a suitable solubility in the organic solvent was added to the formulation. In particular, a calcium carbonate ester available from Troy Chemical Corporation as Calcium 10 was added in three different levels (0.06 wt. %, 0.12 wt. % and 0.18 wt. %) in the formulation, respectively constituting 10:1; 5:1 and 3.3:1 (w:w) of the IPBC to buffer in the formulation. The amount of IPBC remaining after heat aging at 40° C. for 30 days was 78.9%, 82.3% and 83.3% respectively. When contrasted with the result observed for untreated Example 7a (57.7%), the stabilizing effect of the buffer on the formulation, even in the presence of the acidic cobalt drier, is readily apparent.

While certain specific embodiments of the invention have been described with particularity herein, it will be recognized that various modifications thereof will occur to those skilled in the art and it is to be understood that such modifications and variations are to be included within the preview of this application and the spirit and scope of the appended claims.

TABLE 1

| Experiment | Alkyd Low Acid | Alkyd High Acid | Zr Drier 0.06% | Zr Drier 0.23% | Co Drier Acid | Co Drier Base | Order Drier Addition Zr First | Order Drier Addition Co First | MEKO No | MEKO Yes | Response |
|---|---|---|---|---|---|---|---|---|---|---|---|
| 7a | 57.7 | | 57.7 | | 57.7 | | | 57.7 | | 57.7 | 57.7 |
| 7b | 91.3 | | 91.3 | | | 91.3 | | 91.3 | 91.3 | | 91.3 |
| 7c | 62.7 | | | 62.7 | 62.7 | | 62.7 | | | 62.7 | 62.7 |
| 7d | 89.4 | | | 89.4 | | 89.4 | 89.4 | | 89.4 | | 89.4 |
| 7e | | 46.1 | 46.1 | | 46.1 | | 46.1 | | 46.1 | | 46.1 |
| 7f | | 56.6 | 56.6 | | | 56.6 | 56.6 | | | 56.6 | 56.6 |
| 7g | | 53.2 | | 53.2 | 53.2 | | | 53.2 | 53.2 | | 53.2 |
| 7h | | 60 | | 60 | | 60 | | 60 | | 60 | 60 |
| AVERAGE | 75.3 | 54.0 | 62.9 | 66.3 | 54.9 | 74.3 | 63.7 | 65.6 | 70 | 59.2 | 64.6 |
| EFFECT | −21.3 | | +3.4 | | +19.4 | | +1.9 | | −10.8 | | |

TABLE 2

| Experiment | Alkyd Low Acid | Alkyd High Acid | Zr Drier 0.06% | Zr Drier 0.23% | Co Drier Co/Zr | Co Drier Co/Ca | Order Drier Addition Zr First | Order Drier Addition Co First | MEKO No | MEKO Yes | Response |
|---|---|---|---|---|---|---|---|---|---|---|---|
| 7j | | 67.1 | | 67.1 | | 67.1 | 67.1 | | 67.1 | | 67.1 |
| 7j | | 59.1 | | 59.1 | 59.1 | | 59.1 | | | 59.1 | 59.1 |
| 7k | | 65.3 | 65.3 | | | 65.3 | | 65.3 | 65.3 | | 65.3 |
| 7l | | 46.8 | 46.8 | | 46.8 | | | 46.8 | | 46.8 | 46.8 |
| 7m | 87.0 | | | 87.0 | | 87.0 | | 87.0 | 87.0 | | 87.0 |
| 7n | 72.4 | | | 72.4 | 72.4 | | | 72.4 | | 72.4 | 72.4 |
| 7o | 83.3 | | 83.3 | | | 83.3 | 83.3 | | 83.3 | | 83.3 |
| 7p | 67.1 | | 67.1 | | 67.1 | | 67.1 | | | 67.1 | 67.1 |
| AVERAGE | 77.4 | 59.6 | 65.6 | 71.4 | 61.4 | 75.7 | 69.2 | 67.9 | 75.7 | 61.4 | 61.4 |
| EFFECT | −17.8 | | +5.8 | | +14.3 | | −1.3 | | −14.3 | | |

We claim:

1. A biocidal composition comprising a halopropargyl compound and a buffer, wherein the weight ratio of said halopropargyl compound to said buffer is between 50:1 to 1:100 and wherein said composition is useful for providing biocidal activity to an end-use formulation and stabilizing the end-use formulation at a pH of between 3.0 and 8.0 against degradation of said halopropargyl compound.

2. The biocidal composition of claim 1 wherein the halopropargyl compound is an iodopropargyl derivative selected from an iodopropargyl ester, an iodopropargyl ether, an iodopropargyl acetal, an iodopropargyl carbamate and an iodopropargyl carbonate.

3. The biocidal composition of claim 2 wherein the iodopropargyl carbamate has the formula:

where R is selected from the group consisting of hydrogen, substituted and unsubstituted alkyl groups having from 1 to 20 carbon atoms, substituted and unsubstituted aryl, alkylaryl, and aralkyl groups having from 6 to 20 carbon atoms and from substituted and unsubstituted cycloalkyl and cycloalkenyl groups of 3 to 10 carbon atoms.

4. The composition of claim 3 wherein the buffer is selected from the group consisting of bicarbonates, carbonate esters, complex carbonate salts of organic acids, hydrogen phosphates, phosphate esters, phosphinate esters, borates, borate esters, hydrogen sulfates, sulfinates, and sulfate esters.

5. The composition of claim 4 wherein the buffer is selected from the group consisting of potassium bicarbonate, potassium biphthalate, potassium bisulfate, potassium dihydrogen citrate, dipotassium hydrogen citrate, potassium dihydrogen phosphate, dipotassium hydrogen phosphate, potassium hydrogen tartrate, potassium hydrogen oxolate, potassium hydrogen maleate, potassium hydrogen succinate, potassium hydrogen glutarate, potassium hydrogen adipate, potassium tetraborate, potassium pentaborate, potassium octaborate, sodium bicarbonate, sodium biphthalate, sodium bisulfate, sodium dihydrogen citrate, disodium hydrogen citrate, sodium dihydrogen phosphate, disodium hydrogen phosphate, sodium hydrogen tartrate, sodium hydrogen oxolate, sodium hydrogen maleate, sodium hydrogen succinate, sodium hydrogen glutarate, sodium hydrogen adipate, sodium tetraborate, sodium pentaborate, sodium octaborate, complex calcium carbonate salt of octanoic acid, complex calcium carbonate salt of iso-octanoic acid, complex calcium carbonate salt of 2-ethyl hexanoic acid, complex calcium carbonate salt of hexanoic acid, 2-[2-amino-2-oxoethyl)amino]ethanesulfonic acid, N-[2-acetamido]-2-aminoethanesulfonic acid, N,N-bis[2-hydroxyethyl]-2-aminoethanesulfonic acid, 2-[bis(2-hydroxyethyl) amino] ethanesulfonic acid and mixtures thereof.

6. The composition of claim 5 wherein the iodopropargyl carbamate is selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof.

7. The composition of claim 6 wherein the buffer is a complex calcium carbonate salt of iso-octanoic acid.

8. A biocidal composition comprising 3-iodo-2-propynyl butyl carbamate and a buffer, wherein the weight ratio of said 3-iodo-2-propynyl butyl carbamate to said buffer is between 50:1 to 1:100 and wherein said composition is useful for providing biocidal activity to an end-use formulation and stabilizing the end-use formulation at a pH of between 3.0 and 8.0 against degradation of said 3-iodo-2-propynyl butyl carbamate.

9. The biocidal composition of claim 1 wherein the composition is an organic-solvent based composition.

10. The biocidal composition of claim 6 wherein the composition is an organic-solvent based composition.

11. The biocidal composition of claim 7 wherein the composition is an organic-solvent based composition.

12. A method of stabilizing a biocidal formulation containing a halopropargyl compound, said formulation having an alkalinity or an acidity sufficient to cause degradation of said halopropargyl compound in the absence of added acid, base or buffer, said method comprising adding a sufficient amount of an acid, a base or a buffer to said formulation to adjust the pH of said formulation to within the range of 3.0 to 8.0.

13. The method of claim 12 wherein said acid, base or buffer is added in a sufficient amount to adjust the pH of said formulation to a pH in the range of 5.5 to 7.7.

14. The method of claim 13 wherein the halopropargyl compound is an iodopropargyl derivative selected from an iodopropargyl ester, an iodopropargyl ether, an iodopropargyl acetal, an iodopropargyl carbamate and an iodopropargyl carbonate.

15. The method of claim 14 wherein the iodopropargyl carbamate has the formula:

where R is selected from the group consisting of hydrogen, substituted and unsubstituted alkyl groups having from 1 to 20 carbon atoms, substituted and unsubstituted aryl, alkylaryl, and aralkyl groups having from 6 to 20 carbon atoms and from substituted and unsubstituted cycloalkyl and cycloalkenyl groups of 3 to 10 carbon atoms.

16. The method of claim 15 wherein the iodopropargyl carbamate is selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof.

17. An improved method of providing an end-use formulation with biocidal activity comprising adding a sufficient amount of the composition of claim 1 to said end-use formulation to impart biocidal activity to said formulation and provide said formulation with a pH within the range of 3.0 to 8.0.

18. The method of claim 12 wherein the biocidal formulation is an organic-solvent based composition.

19. The method of claim 16 wherein the biocidal formulation is an organic-solvent based composition.

20. The method of claim 17 wherein said composition of claim 1 and said end-use formulation are each an organic-solvent based composition.

21. The composition of claim 8 wherein said biocidal composition and said end-use formulation are each an organic-solvent based composition.

* * * * *